United States Patent [19]  
Noble

[11] 3,992,922  
[45] Nov. 23, 1976

[54] COEFFICIENT OF FRICTIONAL DETERMINING APPARATUS FOR RAILWAY VEHICLES

[75] Inventor: Peter M. Noble, Valencia, Pa.

[73] Assignee: Westinghouse Air Brake Company, Swissvale, Pa.

[22] Filed: Oct. 14, 1975

[21] Appl. No.: 621,944

[52] U.S. Cl. ................................. 73/9; 246/182 A  
[51] Int. Cl.² ........................................ G01N 19/02  
[58] Field of Search ............... 73/9, 122; 246/182 A, 246/182 BH

[56] References Cited  
UNITED STATES PATENTS  
3,033,018   5/1962   Haggadone .............................. 73/9  
3,111,294   11/1963   Werner ...................................... 73/9

Primary Examiner—Donald O. Woodiel  
Attorney, Agent, or Firm—J. B. Sotak; R. W. McIntire, Jr.

[57] ABSTRACT

This disclosure relates to a predictor for determining the coefficient of friction existing between the rotating wheels of moving railway vehicles and the brake shoes of a pair of brake elements prior to the humping operation in a classification. One of the brake elements is slidably mounted to move longitudinally relative to the track rail when engaged by the rotating wheels of the railway vehicle. The kinetic energy or force imparted to the slidable brake element is transposed in fluid pressure by a pressurized responsive transducer. The fluid pressure is sensed by a measuring device which activates an alarm when the wheels of the railway vehicle are dirty or contaminated by unctuous material to permit the vehicle to be diverted to a sidetrack for special handling.

12 Claims, 3 Drawing Figures

DIRECTION OF
TRAVEL OF
RAILROAD CAR

COEFFICIENT OF FRICTIONAL DETERMINING APPARATUS FOR RAILWAY VEHICLES

FIELD OF THE INVENTION

This invention relates to an arrangement for predicting the amount of frictional resistance which will be exhibited by the wheels of moving railway vehicles and more particularly to a coefficient of friction determining apparatus having brake elements for engaging the sides of the wheels of passing railway vehicles and for generating a force which is utilized to determine the coefficient of friction of the passing wheels.

BACKGROUND OF THE INVENTION

In certain railway operations, such as, in the sorting of railway vehicles in hump type of classification or marshalling yards in accordance with consist and destination, it is necessary to control the speed of the free rolling vehicles by suitable braking apparatus. Generally, the braking apparatus takes the form of a frictional car retarder having braking bars which engage and grip the sides of the wheels of the railway vehicles. The amount of braking effort which is to be exerted on the wheels of the railway vehicles by the car retarder is dependent upon the rollability and the distance that the humped vehicle has to go to couple with the previous vehicle in the appropriated class track. In order to prevent damage to the railway vehicles upon coupling, it is necessary to ensure that the leaving speed of the vehicle from the car retarder is not excessive. That is, if the differential velocity between the coupling vehicles is greater than a given value, the ensuing collision can cause derailments and damage to the railway cars and can impair the lives of workmen and other individuals in the area. Normally, the leaving speeds of the humped vehicles is quite accurately and effectively controlled by the car retarders to permit smooth and safe coupling. However, the finds of two recent costly and tragic accidents in two different classification yards have shown that the car retarders were unable to effectively frictionally brake the wheels of certain railway cars. The two accidents involved tank cars carrying volatile hydrocarbon gases, such as propylene, propane, methane, ethane, ethylene and other hydrocarbons which were released to the atmosphere when the tankers were punctured upon collision. The leaking hydrocarbon gases were ignited by a stray spark which caused a tremendous explosion and resultant fire. One of the explosions caused more than (230) persons to be injured and resulted in (7½) million dollars in estimated property damage. The other explosion caused an estimated (30) million dollars of property damage, resulted in approximately (300) personal injuries and caused at least one death. When the fire was extinguished and the smoke had cleared, a post-accident examination revealed that the wheels of the cars which caused the collisions were covered with a slippery foreign substance, namel, heavy grease in the first case and epoxy resin in the second case which prevented effective retardation of free rolling cars. It will be appreciated that grease, oil, and other foreign unctuous material on the wheels of humped cars cause the brake shoes of the car retarders to become ineffective in decelerating and slowing down the humped cars to a safe coupling speed. In order to positively prevent any further tank car explosions in classification yards, the Federal Railroad Administration (FRA) has invoked Emergency Order No. 5 which requires that all cars carrying explosive lading, such as, liquid petroleum gas (LPG) and the like, must be moved and classified by a locomotive or engine and that the following car in that class track must also be handled by a locomotive. The approximate annual cost of handling the explosive cars and the follow-up cars by yard locomotives is estimated at more than (55) million dollars. While the exorbitant cost of handling of explosive carrying cars by locomotives appears justified from the standpoint of protecting the life and limb of innocent people, it is obviously not the ultimate solution. It would be less costly, less time consuming and more efficient to readily ascertain the condition of wheels of the railway cars prior to humping in order to prevent possible explosions yet expedite the classification of trains. Thus, it is very desirable and highly advantageous to substantially eliminate or minimize the number of hazardous tank cars that are required to be handled by yard engines during classification by determining the coefficient of friction that will exist between the sides of the wheels of the railway cars and the brake shoes prior to humping. That is, as each of the railway vehicles approaches the hump, it is necessary to predicate whether or not the railway vehicle will be decelerated by the hump and group car retarders. If the wheels of the vehicle are clean or uncontaminated, a high coefficient of friction will exist thereby ensuring that sufficient retardation is effected to reduce the speed of the vehicles to a safe coupling speed; however, if the wheels of the vehicle are dirty or contaminated with grease, oil, paint, lading spillage or slippery foreign material, a relatively low coefficient of friction will exist thereby preventing effective retardation and resulting in the vehicle leaving the car retarder at an excessive unsafe coupling speed.

OBJECTS OF THE INVENTION

Accordingly, it is an object of this invention to provide a novel coefficient of friction determining mechanism for predicting the amount of retardation that can be exerted on the sides of wheels of railway vehicles.

A further object of this invention is to provide unique mechanism for determining the coefficient of friction of moving objects.

Another object of this invention is to provide apparatus for predicting the frictional resistance of the wheels of railway cars.

Yet a further object of this invention is to provide a coefficient of friction determining arrangement for ascertaining whether the wheels of a railway vehicle will undergo sufficient retardation if humped in a classification yard.

Still another object of this invention is to provide a coefficient of friction predicting mechanism for determining whether a car retarder can sufficiently brake a moving railway vehicle.

Yet a further object of this invention is to provide a frictional gripping mechanism for predicting the condition of the wheels of railway vehicles prior to humping.

Still another object of this invention is to provide a coefficient of friction determining mechanism including means for frictionally engaging passing wheels of railway vehicles and for developing a force in at least one direction and having means responsive to the force for determining the coefficient of friction of the passing wheels of the railway vehicles.

An additional object of this invention is to provide a coefficient of friction predicting arrangement which is economcial in cost, simple in construction, easy to install, dependable in service, durable in use and efficient in operation.

SUMMARY OF THE INVENTION

In accordance with the present invention there is provided a coefficient of friction predicting arrangement for determining the amount of retardation that will occur between the wheels of railway vehicles and the brake shoes of a car retarder prior to humping the railway vehicles. The arrangement includes a pair of mechanisms each of which is disposed relative to the respective rail of the trackway leading to the hump in a classification yard. Each mechanism includes operating units each having an actuator and a pair of pivotal levers. One of the pivotal levers carries an outer brake element while the other pivotal lever carries an inner brake element. The inner and outer brake elements are movable between an open nonbraking or non-measuring position and a closed braking or measuring position by pivotal movement of the levers which are operated by the actuators. Each of the brake elements includes an elongated brake beam and an elongated brake show which engages the respective sides of the wheels of railway cars when in the closed braking position. The inner brake element is slidably journaled on bar members which are fixedly mounted parallel to the track rails. The frictional engagement of the wheels of the railway cars with the brake shoe causes the slidable inner brake element to move in the direction of the traversing railway car. The slidable inner brake element cooperates with and forces the pitson into the cylinder of a pressure responsive tranducer. A pressure source including a motor and pump supplies hydraulic pressure to the cylinder through a pressurized pneumatic-hydraulic reservoir. A pressure sensitive device which operates a measuring device and in turn an associated alarm is connected to the cylinder of the pressure responsive transducer. The predictor is in a quiescent state when in the open nonbraking braking position since the wheels do not engage the brake shoes so that the moving railway vehicle is permitted to freely pass. When the predictor is activated by applying pneumatic pressure to the actuators of the operating units, the levers lift and close the brake elements so that the brake shoes come in frictional contact with the sides of the passing wheels of the railway vehicle. The rotating wheels cause a longitudinal force to be imparted to the slidable brake elements with the result that the elements move parallel to the track rail. The longitudinal movement of the brake elements is conveyed to the piston of the hydraulic transducer, and the amount of force exerted on the piston is directly proportional to the frictional drag existing between the wheels and the brake shoe. Thus, the pressure developed in the cylinder of the pressure responsive transducer is proportional to the coefficient of friction of the wheels traversing the predictor. When the wheels are clean or uncontaminated, the coefficient of friction is relatively high so that an elevated pressure is sensed by the pressure sensitive device and measuring device exhibits a relatively large output and the alarm is silent. Thus, the railway car is permitted to be humped in the normal manner. However, when the wheels of a railway car are dirty, or contaminated by oil, grease, lading spillage or the like, the coefficient of friction is relatively low so that a relatively low pressure is developed by the pressure responsive transducer, and the output of the measuring device is very low or zero. This causes the alarm to be sounded so that the yard personnel may take appropriate action to sidetrack the contaminated vehicle before it reaches the hump. Accordingly, with the present invention it is possible to effectively predict whether or not a railway car will be sufficiently decelerated by a frictional car retarder prior to humping in order to prevent damage to lading and preclude explosion of hazardous laden tank cars.

BRIEF DESCRIPTION OF THE DRAWINGS

The foregoing objects and other attendant features and advantages of this invention will become more fully evident from the following detailed description when analyzed and considered in conjunction with the accompanying drawings wherein.

DESCRIPTION OF THE INVENTION

Figure 1:
FIG. 1 is a top plan view showing a dual track coefficient of friction predicting apparatus in accordance with the present invention.

Referring now to the drawings and in particular to FIG. 1, there is shown a section of trackway TR leading to the hump of the classification yard. The trackway section TR includes a left-hand rail LR and a right-hand RR as seen in FIG. 1. As shown, the coefficient of friction predicting or determining apparatus is disposed about both rails so that both wheels of each axle of the railway vehicles may be inspected or analyzed as the vehicles are pushed toward the hump area. As shown, the predictor includes a pair of mechanisms LM and RM, one of which is disposed about track rail LR and the other of which is disposed about track rail RR. The track rails are secured to a plurality of rail supports of chairs RS (see FIG. 2) mounted on the usual crossties in a conventional manner. The mechanisms LM and RM are substantially identical in construction and therefore for the purposes of convenience only one of the mechanisms will be described in detail.

Figure 2:
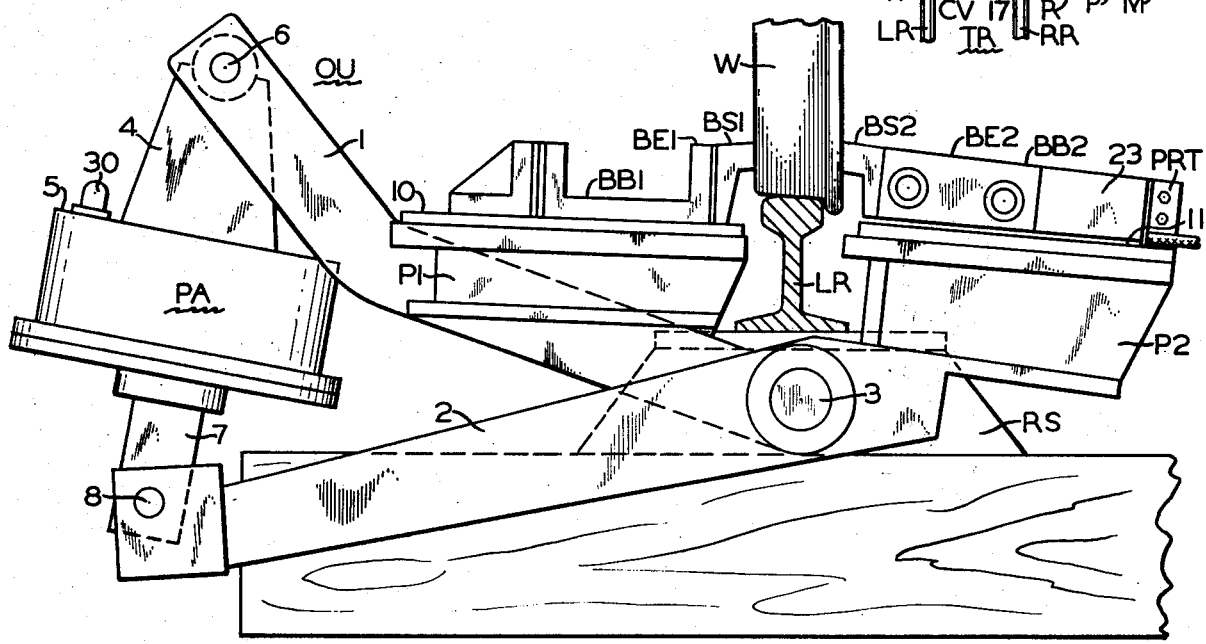
FIG. 2 is an enlarged vertical sectional view of an operating unit for the coefficient of friction predicting apparatus taken substantially along line II—II of FIG. 1.

In viewing FIGS. 1 and 2, it will be seen that each mechanism of the coefficient of friction predictor includes operating units OU. Each operating unit comprises an upper pivotal lever 1 and a lower pivotal lever 2. A pivot pin 3 cooperates with reinforced bearing apertures located intermediate the ends of both levers to rotatably support the levers in relation to each other. The outer end of the upper lever 1 is inclined upwardly and extends away from rail LR and is pivotally connected to the attachment bracket 4 of cylinder 5 of a fluid motor or pneumatic pressure actuator PA by pivot pin 6. The outer end of the lower lever 2 is slightly inclined downwardly and also extends away from rail LR and is pivotally connected to the piston rod 7a of piston 7b of the actuator PA by pivot pin 8. The intermediate portion of the upper lever 1 of each of the operating units OU is provided with a fabricated weldment pedestal P1 having an upper flat surface 10 which supports brake elements BE1. Likewise, the free end of the lower pivotal lever 2 of each of the operating units OU is provided with a fabricated weldment pedestal P2 having an upper flat surface 11 for accommodated brake element BE2. It will be noted in FIG. 1, that the brake elements BE1 and BE2 are disposed on opposite sides of the rails LR and RR.

Figure 3:
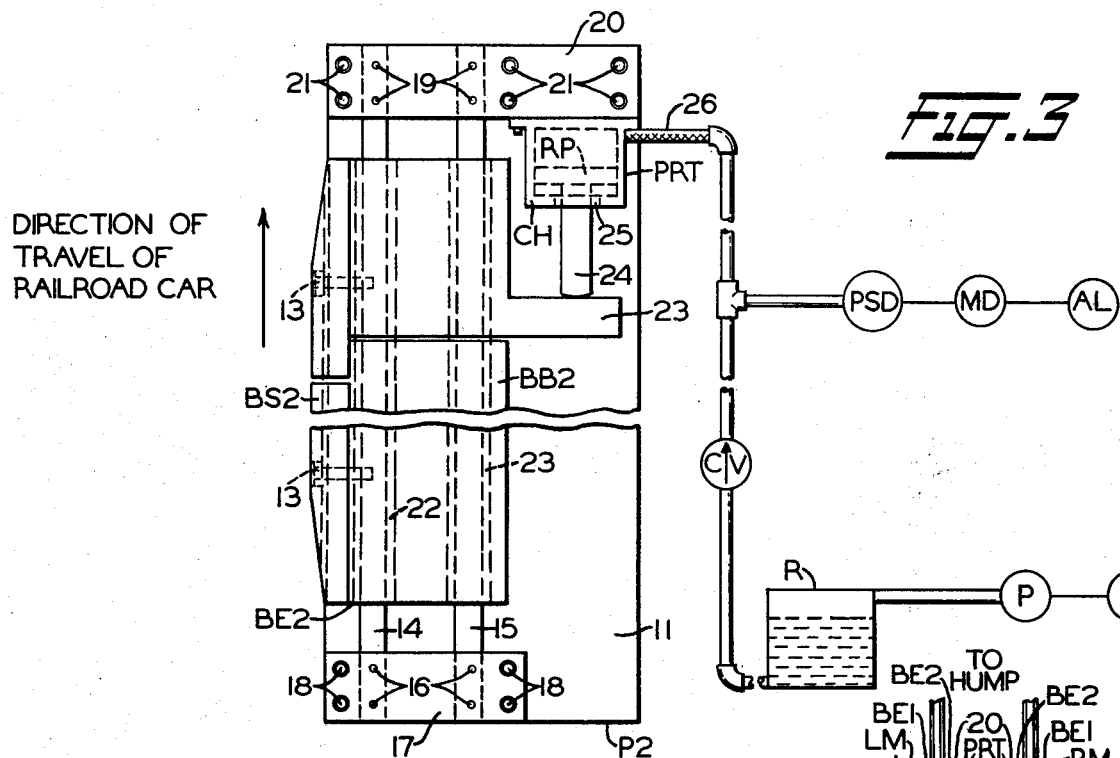
FIG. 3 is a partial top plan view of the movable brake element and the various circuit elements of the left-handed track section as viewed in FIG. 1.

The inner and outer brake elements BE1 and BE2 which are carried by the upper and lower levers 1 and 2 extend parallel to the rails LR and RR to form a pair of elongated members. The outer brake element BE1 includes an elongated brake beam BB1 and a replaceable elongated brake shoe BS1 while the inner brake element BE2 includes an elongated brake beam BB2 and a replaceable elongated brake shoe BS2. Usually, the brake beams and brake shoes are fabricated in sections or lengths to facilitate initial assembly and subsequent replacement. The brake beam BB1 is suitably secured to the pedestal P1 by appropriate fasteners, such as bolts and nuts (not shown). Likewise, the replaceable brake shoe BS1 is fixedly attached to the brake beam BB1 by suitable fasteners, such as bolts and nuts (not shown). In viewing FIGS. 2 and 3, it will be noted that the brake shoe BS2 is secured to the brake beam BB2 bolts 13 which are countersunk. The brake shoe BS2 is tapered at each end to permit smooth entry and exit of the wheel W of the railway vehicle. It will be noted that the brake element BE2 is slidably mounted on a pair of steel bars or rods 14 and 15 to permit longitudinal movement relative to the length of the rail LR. One end of the bars 14 and 15 is fixedly secured by set screw 16 or the like to a retaining block 17 which is securely fastened to the top of pedestal P2 by a plurality of machine bolts 18. Likewise, the other end of the steel bars 14 and 15 is fixedly secured by set screws 19 or the like to the retaining block 20 which is securely fastened to the top of pedestal P2 by a plurality of machine bolts 21. Thus, the slide bars 14 and 15 are mounted parallel to the rail, and the brake beam BB2 includes sleeve bearings 22 and 23 which are fitted and journaled on the steel bars 14 and 15, respectively. As shown in FIGS. 2 and 3, the brake element BE2 is disposed intermediate the two retaining blocks 17 and 20, and the brake beam BB2 is provided with a perpendicular extend portion or arm 23 which cooperates and engages the piston rod 24 of a hydraulic pressure responsive transducer PRT.

In viewing FIG. 3, it will be seen that the pressure responsive transducer PRT includes a cylinder housing CH which receives a reciprocating piston RP. The piston rod 24 which is securely attached to the piston RP passes through a suitable opening in the front end of the housing CH which includes an appropriate sealing member or ring 25. The back end of the cylinder housing CH includes a flange which is bolted or securely fixed to the retaining block 20 for holding the transducer PRT in proper relationship with the arm 23. A flexible conduit or hose 26 is threadedly connected to a suitable threaded opening or hole formed in the side of the cylinder housing CH. The flexible hose is coupled through appropriate conduit, fittings and a check valve CV to a pneumatic-hydraulic accumulator or reservoir R. The check valve CV readily permits the forward flow of hydraulic fluid from the reservoir R as shown by the arrow but blocks the reverse flow of fluid to the reservoir R. The reservoir R is kept under constant pressure by the electric motor M and pneumatic pump P which supplies air and pressurizes the top of the reservoir R. As shown, a suitable pressure sensitive device PSD is coupled through a tee and hydraulic conduit to sense the pressure level in the hydraulic system. The pressure sensitive device PSD which may be a diaphragm or bellows operated device or the like, is coupled to a pressure measuring device MD which in turn is coupled to an appropriate alarm AL.

It will be understood that the parts are so arranged and proportioned that when the outer ends of pivotal levers 1 and 2 are moved apart by application of air pressure to the power actuator PA, the brake elements BE1 and BE2 will be moved upwardly and toward the rail LR to the effective braking position in which the brake shoes BS1 and BS2 assume a closed position as shown in FIG. 2 whereby they frictionally engage the opposite sides of the wheel W. The center of gravity of the upper lever 1 and the brake element BE1 is considerably to the left of the pivot 3, as will be observed from FIG. 2, so that lever 1 will normally tend to rotate in a counterclockwise direction relative to the pivot pin 3. It will be seen that the center of gravity of the lower lever 2 and the brake element BE2 is to the right of the pivot pin 3, as viewed in FIG. 2, so that lever 2 will normally tend to swing in a clockwise direction relative to the pivot pin 3. Thus, when no pressure force is applied to the outer ends of the levers 1 and 2 to move them apart, the outer free ends of the levers will move toward each other, thereby moving the brake elements downwardly and away from the respective rails to their open or ineffective position whereby the wheel of a railway car is permitted to pass freely without engagement.

As mentioned above, levers 1 and 2 are arranged to be moved apart by means of a conventional fluid pressure motor or actuator PA comprising a cylinder 5 containing piston rod 7 and an attached piston (not shown). When it is desired to measure and determine the coefficient or friction of the wheels of the cars of an incoming train which is to be humped, fluid pressure may be admitted to the cylinder 5 through an opening which is threaded to receive fitting 30. In operation when air pressure is admitted to the cylinder 5, a downward force is exerted on the piston and an upward force is exerted on the cylinder 5, thereby separating the arms of the levers 1 and 2. As the levers move apart, the lever 1 will rotate in a clockwise direction about fulcrum pin 3 while the lever 2 will rotate in a counterclockwise direction about fulcrum pin 3. The clockwise rotation of lever 1 causes the brake element BE1 to move upwardly and inwardly relative to the rail while the counterclockwise rotation of the lever 2 causes the brake element BE2 to move upwardly and inwardly relative to the rail so that the predictor assumes a position as shown in FIG. 2. Now as the railway vehicle, such as, a hazardous gas carrying tank car, approaches the predictor area, the wheels smoothly enter and engage the brake shoes BS1 and BS2 due to their tapered ends. As the opposite sides of the rotating wheels frictionally engage the brake shoes BS1 and BS2, a lateral force is imparted to the brake elements BE1 and BE2. The brake element BB1 remains stationary since it is securely fastened to the pedestal P1 and in turn to the uppper lever 1 of the operating unit OU. However, the lateral force causes the brake element BE2 to move longitudinally on the slide bars 14 and 15 along the length of the rail LR. The longitudinal movement of the brake element BE2 causes the arm portion 23 to act on and depress piston rod 24 and piston RP into the cylinder CH. Thus, the force is transposed into pressure which is conveyed from transducer PRT to the pressure sensitive device PSD. Initially, the pressure sensitive device PSD is set to correspond to a value by the reservoir R which is just sufficient for proper car control by the car retarders. Thus, if the kinetic energy or force developed by the brake element BE2 and the pressure produced in the pressure responsive transducer PRT and sensed by the pressure sensitive device PSD is greater than the initial set value, then the car retarder control will respond normally. Hence, the output of the measuring device MD will indicate that the coefficient of friction is sufficiently high to allow for adequate retardation and control of the car when humped. Under this condition, the alarm AL is silent since the measuring device responds to the fact that the wheel of the railway vehicle is clean and exhibits a relatively high coefficient of friction.

However, if the kinetic energy or force developed by the brake element BE2 and the pressure produced in the pressure responsive transducer is less than that which is considered the normal and required coefficient of friction value, then the car retarder will be incapable of sufficiently retarding the railway vehicle because the wheels are dirty and contaminated by grease, oil, or the like. Thus, the measuring device MD will produce an output signal which is indicative of the low coefficient of friction of the dirty wheels and will cause the alarm AL to be sounded. The alarm will alert the yardmaster, the hump conductor and/or other appropriate personnel of the contaminated condition of the railway car so that the car may be switched to a siding or sidetrack for individual or special handling. Thus, the predictor determines the physical condition of the wheels of the railway cars prior to humping to positively ensure that a contaminated car will not be allowed to run away and cause an accident or explosion in a hump type of railroad classification yard. It will be appreciated after the disengagement of each wheel of each railway car the movable brake element BE1 is returned to its initial position by the piston rod 24 since the transducer PRT is constantly pressurized by the reservoir R.

It will be understood that various changes, modifications and alterations may be made to the illustrated and described embodiment without departing from the spirit and scope of the present invention.

For exammple, the movement and force produced on the movable brake element BE2 by the wheels may be changed to a vertical direction rather than a horizontal direction or the force measured in any and all directions, horizontal, vertical, angular, etc., may be employed in practicing the invention. Additionally, it is understood that the outer brake element BB1 may be longitudinally moved rather than element BB2, or both elements may be utilized in the predication and measurement. Further, the hydraulic pressure responsive and sensing apparatus may be replaced by strain gauges, accelerometers or temperature sensing devices or the like to determine the coefficient of friction of the wheels. In addition, it will be understood that the measuring device may take the form of an analog or digital device which may be interfaced with the automatic control apparatus of a computer controlled classification yard to exactly determine the degree of retardation that each vehicle will undergo during classification. Further, the alarm AL may be audio or visual or both and may require acknowledgment by the yardmaster or other responsible person. Other substitutions and ramifications will undoubtedly occur to those skilled in the art that are deemed to fall within the preview of the present invention which is intended to be limited only as set forth in the appended claims. Thus, it is understood that the showing and description of the present invention should be taken as illustrative or diagrammatic sense only.

Having now described the invention what I claim as new desire to secure by Letters Patent is:

1. A coefficient of friction determining arrangement comprising, means for frictionally engaging the sides of passing wheels of railway vehicles and for developing a force in at least one direction, and means responsive to said force for determining the coefficient of friction existing between said frictional engaging means and the passing wheels of the railway vehicles.

2. A coefficient of friction determining arrangement comprising, means for frictionally engaging passing wheels of railway vehicles and for developing a force in at least one direction, said wheel engaging means including an elongated brake beam and brake shoe disposed on either side of a running rail for engaging the sides of the passing wheels of the railway vehicles and for urging at least one of said elongated brake beam and brake shoe to be displaced a given amount, and means responsive to said force for determining the coefficient of friction existing between said frictional engaging means and the passing wheels of the railway vehicles.

3. The arrangement as defined in claim 2, wherein said given amount of displacement of said elongated brake beam and brake shoe operates a hydraulic responsive means.

4. The arrangement as defined in claim 3, wherein said hydraulic responsive means includes a piston and a cylinder which are moved relative to each other by the displacement of said brake beam and brake shoe.

5. The arrangement as defined in claim 3, wherein a source of pneumatic pressure is connected to a reservoir which supplies hydraulic fluid to said hydraulic responsive means.

6. The arrangement as defined in claim 3, wherein said hydraulic responsive means includes a pressure sensitive device.

7. Apparatus for predicting the coefficient of friction of moving objects comprising, means for supporting and guiding the moving objects along a path of travel, means disposed at a predetermined location along said path of travel and movable into frictional gripping engagement with the moving objects for producing a force in a given direction, and means actuated by said force for providing a low coefficient of friction indication due to the moving objects being contaminated by slippery foreign material.

8. A coefficient of friction determining arrangement comprising, means for frictionally engaging passing wheels of railway vehicles and for developing a force in at least one direction, said wheel engaging means including an elongated brake element located on each side of each track rail for gripping the sides of the passing wheels of the railway vehicles, and means responsive to said force for determining the coefficient of friction existing between the frictional engaging means and the passing wheels of the railway vehicles.

9. The arrangement as defined in claim 8, wherein at least one elongated braking element is slidably journaled on a pair of slide bars which are mounted parallel to the track rail.

10. A coefficient of friction determining arrangement comprising, means for frictionally engaging passing wheels of railway vehicles and for developing a force in at least one direction, means responsive to said force for determining the coefficient of friction existing between said frictional engaging means and the passing wheels of the railway vehicles, and said responsive means including a pressure sensitive device which provides an indication proportional to said force.

11. A coefficient of friction determining arrangement comprising, means for frictionally engaging passing wheels of railway vehicles and for developing a force in at least one direction, said wheel engaging means including pivotal levers and an actuating mechanism for urging elongated braking bars into engagement with the sides of the passing wheels of the railway vehicles, and means responsive to said force for determining the coefficient of friction existing between said frictional engaging means and the passing wheels of the railway vehicles.

12. A coefficient of friction determining arrangement comprising, means for frictionally engaging passing wheels of railway vehicles and for developing a force in at least one direction, means responsive to said force for determining the coefficient of friction existing between said frictional engaging means and the passing wheels of the railway vehicles, and a warning means is actuated when the coefficient or friction between frictional engaging means and the passing wheels of the railway vehicles is below a predetermined amount.

* * * * *